US011702397B2

(12) United States Patent
Thomas et al.

(10) Patent No.: US 11,702,397 B2
(45) Date of Patent: *Jul. 18, 2023

(54) METHODS TO PURIFY CANNABINOIDS

(71) Applicant: Natural Extraction Systems, LLC, Boulder, CO (US)

(72) Inventors: C. Russell Thomas, Boulder, CO (US); Matthew M. DePalo, Wheat Ridge, CO (US)

(73) Assignee: NATURAL EXTRACTION SYSTEMS, LLC, Boulder, CO (US)

( * ) Notice: Subject to any disclaimer, the term of this patent is extended or adjusted under 35 U.S.C. 154(b) by 408 days.

This patent is subject to a terminal disclaimer.

(21) Appl. No.: 17/086,693

(22) Filed: Nov. 2, 2020

(65) Prior Publication Data

US 2021/0106929 A1 Apr. 15, 2021

Related U.S. Application Data

(63) Continuation of application No. 16/271,783, filed on Feb. 9, 2019, now Pat. No. 10,822,320.

(60) Provisional application No. 62/803,409, filed on Feb. 8, 2019, provisional application No. 62/717,235, filed on Aug. 10, 2018.

(51) Int. Cl.
*C07D 311/78* (2006.01)
*B01D 17/06* (2006.01)
*B01D 5/00* (2006.01)
*C07D 311/80* (2006.01)

(52) U.S. Cl.
CPC ............ *C07D 311/78* (2013.01); *B01D 17/06* (2013.01); *B01D 5/006* (2013.01); *B01D 2257/70* (2013.01); *C07D 311/80* (2013.01)

(58) Field of Classification Search
CPC ....... C07D 311/78; C07D 11/80; C07D 11/78; B01D 5/006; B01D 17/06
See application file for complete search history.

(56) References Cited

U.S. PATENT DOCUMENTS

| | | | |
|---|---|---|---|
| 2,467,435 A | 4/1949 | Langhurst | |
| 2,805,981 A | 9/1957 | Cavin | |
| 3,270,437 A | 9/1966 | Lara | |
| 4,227,997 A | 10/1980 | Shaddock | |
| 4,279,824 A | 7/1981 | McKinney | |
| 4,396,487 A | 8/1983 | Strumskis | |
| 4,752,307 A | 6/1988 | Asmus | |
| 5,002,784 A | 3/1991 | Paré | |
| 5,026,549 A | 6/1991 | Coutiere | |
| 5,235,992 A | 8/1993 | Sensabaugh, Jr. | |
| 5,408,924 A | 4/1995 | Arendt | |
| 5,458,897 A | 10/1995 | Paré | |
| 6,019,819 A | 2/2000 | Williams | |
| 6,248,910 B1 | 6/2001 | Franke | |
| 6,403,126 B1 | 6/2002 | Webster | |
| 6,860,998 B1 | 3/2005 | Wilde | |
| 7,001,502 B1 | 2/2006 | Satchwell | |
| 7,001,629 B1 | 2/2006 | Mengal | |
| 7,344,736 B2 | 3/2008 | Whittle | |
| 7,622,140 B2 | 11/2009 | Whittle | |
| 7,833,298 B2 | 11/2010 | Larnholm | |
| 8,062,410 B2 | 11/2011 | Bullinger | |
| 8,329,229 B2 | 12/2012 | Gonzalez | |
| 8,343,553 B2 | 1/2013 | Hospodor | |
| 8,445,034 B1 | 5/2013 | Coles, Jr. | |
| 9,038,413 B2 | 5/2015 | Howard | |
| 9,987,567 B1 | 6/2018 | Ko | |
| 10,159,908 B2 | 12/2018 | Thomas | |
| 10,195,159 B2 | 2/2019 | Whittle | |
| 10,238,705 B2 | 3/2019 | Speier | |
| 10,456,708 B2 | 10/2019 | Thomas | |
| 10,617,974 B2 | 4/2020 | Thomas | |
| 10,669,248 B2 | 6/2020 | Thomas | |
| 10,822,320 B2 | 11/2020 | Thomas et al. | |
| 11,021,674 B2 | 6/2021 | Thomas | |
| 2002/0139097 A1 | 10/2002 | Brilmaker | |
| 2004/0049059 A1 | 3/2004 | Mueller | |
| 2004/0147767 A1 | 7/2004 | Whittle | |
| 2004/0147769 A1 | 7/2004 | Davis | |
| 2004/0187340 A1 | 9/2004 | Chemat | |
| 2005/0042172 A1 | 2/2005 | Whittle | |
| 2005/0172802 A1 | 8/2005 | Betting | |
| 2009/0054711 A1 | 2/2009 | Lawrence | |
| 2010/0119606 A1 | 5/2010 | Whittle | |
| 2011/0133120 A1 | 6/2011 | McGhee | |
| 2012/0012002 A1 | 1/2012 | Kaneko | |
| 2012/0157719 A1 | 6/2012 | Teles | |
| 2013/0240347 A1 | 9/2013 | Hackleman | |
| 2014/0001027 A1 | 1/2014 | Balass | |
| 2014/0113010 A1 | 4/2014 | Hospodor | |

(Continued)

FOREIGN PATENT DOCUMENTS

CA 2472561 A1 8/2002
CN 201643760 U 11/2010

(Continued)

OTHER PUBLICATIONS

Wang et al., Cannabis and Cannabinoid Research, vol. 1.1, pp. 262-271 (2016).
Kanter et al., "Qualitative determination of delta9-tetrahydrocannabinol and delta9-tetrahydrocannabinolic acid in marihuana by high-pressure liquid chromatograph," Journal of Chromatography, 1979, pp. 504-508, vol. 171.
Veress et al., "Determination of cannabinoid acids by high-performance liquid chromatography of their neutral derivatives formed by thermal decarboxylation: I. Study of the decarboxylation process in open reactors," Journal of Chromatography, 1990, pp. 339-347, vol. 520.
Benmoussa, H. et al. Enhanced solvent-free microwave extraction of Foeniculum vulgare Mill. essential oil seeds using double walled reactor. Arabian Journal of Chemistry (2019) 12, 3863-3870.

(Continued)

*Primary Examiner* — Noble E Jarrell
(74) *Attorney, Agent, or Firm* — Holland & Hart LLP

(57) ABSTRACT

Various aspects of this patent document relate to the rapid purification of cannabinoids by vaporization and condensation.

20 Claims, 1 Drawing Sheet

(56) References Cited

U.S. PATENT DOCUMENTS

| | | |
|---|---|---|
| 2014/0193303 A1 | 7/2014 | Ellis |
| 2014/0271940 A1 | 9/2014 | Wurzer |
| 2015/0068113 A1 | 3/2015 | Conner |
| 2015/0252286 A1 | 9/2015 | Scialdone |
| 2016/0038437 A1 | 2/2016 | Whittle |
| 2016/0053199 A1 | 2/2016 | Clodoveo |
| 2018/0000857 A1 | 1/2018 | Kotra et al. |
| 2018/0078874 A1 | 3/2018 | Thomas |
| 2018/0296617 A1 | 10/2018 | Rivas |

FOREIGN PATENT DOCUMENTS

| | | |
|---|---|---|
| CN | 101553702 B | 6/2012 |
| CN | 105943615 A | 9/2016 |
| EP | 2644039 A1 | 10/2013 |
| EP | 3453397 A1 | 3/2019 |
| FR | 2742358 A1 | 6/1997 |
| GB | 635121 | 4/1950 |
| GB | 2372714 A | 9/2002 |
| JP | 4388715 B2 | 11/2002 |
| JP | 4849578 B1 | 1/2012 |
| WO | 2002089945 A2 | 11/2002 |
| WO | WO 2007/041167 * | 4/2007 |
| WO | 2014000077 A1 | 1/2014 |
| WO | 2015049585 A2 | 4/2015 |
| WO | 2016153347 A1 | 9/2016 |
| WO | 2016161420 A1 | 10/2016 |
| WO | 2018009514 A1 | 1/2018 |

OTHER PUBLICATIONS

Filly, A. et al., Solvent-free microwave extraction of essential oil from aromatic herbs: From laboratory pilot industrial scale. Food Chemistry 150(2014); 193-198.

Petrov, V.M. et al. Microwave Absorbing Materials. Inorganic Materials vol. 37, No. 2, 2001, pp. 93-98.

Wang, Z. et al. Improved solvent-free microwave extraction of essential oil from dried *Cuminum cyminum* L. and *Zanthoxylum bungeanum* Maxim. Journal of Chromatography A, 1102 (2006) 11-17.

\* cited by examiner

METHODS TO PURIFY CANNABINOIDS

PRIORITY CLAIM

This patent application claims priority to U.S. Provisional Patent Application No. 62/717,235, filed Aug. 10, 2018, U.S. Provisional Patent Application No. 62/803,409 filed Feb. 8, 2019, and U.S. patent application Ser. No. 16/271,783, filed Feb. 9, 2019, which granted as U.S. Pat. No. 10,822,320, each of which is incorporated by reference in its entirety.

BACKGROUND

Industrial hemp and other forms of *cannabis* contain a variety of different cannabinoids, which predominantly each contain a carboxyl group. These cannabinoid carboxylic acids bind the human cannabinoid receptors with relatively low affinity. The production of therapeutic pharmaceuticals and psychoactive drugs from *cannabis* therefore generally utilizes a decarboxylation step, which typically involves prolonged heating. This heating also generally introduces other chemical modifications that are typically undesirable.

Marijuana produces tetrahydrocannabinolic acid ("THCA"), for example, which lacks robust pharmacological effects. THCA is converted into the psychoactive molecule tetrahydrocannabinol ("THC") by decarboxylation, which occurs when marijuana is smoked. THC is commercially produced from THCA by heating the THCA for several hours. Prolonged heating nevertheless results in undesirable side products. THCA can be oxidized, for example, into cannabinolic acid ("CBNA"), which decomposes into cannabinol ("CBN"). CBNA lacks well-known pharmacological properties, and CBN causes drowsiness.

Industrial hemp similarly produces cannabidiolic acid ("CBDA"), which lacks robust pharmacological effects. CBDA is converted into the pharmaceutical cannabidiol ("CBD") by decarboxylation. CBD is commercially produced from CBDA by heating the CBDA for several hours. Prolonged heating nevertheless results in undesirable side products including CBN.

The industrial production of decarboxylated cannabinoids also degrades and vaporizes other molecules found in *cannabis* including terpenes, terpene alcohols, terpenoids, and flavonoids, which often impart favorable characteristics to products containing cannabinoids including favorable flavor and aroma.

Improved methods to decarboxylate cannabinoids are desirable.

SUMMARY

Various aspects of this patent document relate to a method to purify tetrahydrocannabinol from a non-volatile molecule, comprising: (1) providing a composition comprising tetrahydrocannabinol and a non-volatile molecule, wherein both the tetrahydrocannabinol and the non-volatile molecule are in a liquid phase; (2) contacting the composition with energy to convert the tetrahydrocannabinol in the liquid phase into vaporized tetrahydrocannabinol in a gas phase without vaporizing the non-volatile molecule; (3) separating the vaporized tetrahydrocannabinol in the gas phase from the non-volatile molecule; (4) contacting the vaporized tetrahydrocannabinol with a heat sink to condense the vaporized tetrahydrocannabinol into condensed tetrahydrocannabinol in a liquid distillate that comprises (i) the condensed tetrahydrocannabinol and cannabinol at a molar ratio greater than 100:1, and (ii) the condensed tetrahydrocannabinol and delta-8-tetrahydrocannabinol at a molar ratio greater than 300:1; and (5) collecting the liquid distillate.

In some embodiments, the method comprises contacting the composition with a heated surface having a temperature of at least 105 degrees Celsius and no greater than 260 degrees Celsius. In some specific embodiments, the method comprises contacting the composition with a heated surface having a temperature of at least 170 degrees Celsius and no greater than 230 degrees Celsius. In some very specific embodiments, the method comprises contacting the composition with a heated surface having a temperature of at least 210 degrees Celsius and no greater than 230 degrees Celsius.

In some embodiments, the method comprises coating the heated surface with the composition at a surface-area-to-volume ratio of the composition that is greater than 500 per meter.

In some embodiments, the method comprises contacting the composition with less than 100 kilowatts of power per gram of the composition. In some specific embodiments, the method comprises contacting the composition with at least 50 watts and no greater than 500 watts of power per gram of the composition. In some very specific embodiments, the method comprises contacting the composition with at least 300 watts and no greater than 500 watts of power per gram of the composition.

In some embodiments, the method comprises contacting the composition at least 1 kilojoules and no greater than 5 kilojoules of energy per gram of the composition. In some specific embodiments, the method comprises contacting the composition at least 3 kilojoules and no greater than 5 kilojoules of energy per gram of the composition.

In some embodiments, the method comprises conductively heating the composition in an oven, retort, distillation still, falling film evaporator, or short-path distillation apparatus.

In some embodiments, the method comprises coating a surface of a short-path distillation apparatus with the composition at a surface-area-to-volume ratio of the composition that is greater than 500 per meter.

In some embodiments, the method comprises contacting the vaporized tetrahydrocannabinol with the heat sink less than 360 seconds after converting the tetrahydrocannabinol in the liquid phase into the vaporized tetrahydrocannabinol in the gas phase In some embodiments, the non-volatile molecule is chlorophyll, cellulose, a nucleic acid, a protein, a carbohydrate, a sugar, a triglyceride, a phospholipid, a fatty acid, a salt, or an ion.

In some embodiments, the method comprises producing a liquid distillate comprising tetrahydrocannabinol at a concentration of at least 70 percent and no greater than 95 percent by weight. In some specific embodiments, the method comprises producing a liquid distillate that comprises: (1) cannabidiol at a concentration of at least 0.5 percent and no greater than 25 percent by weight; (2) tetrahydrocannabivarin at a concentration of at least 0.5 percent and no greater than 25 percent by weight; and (3) tetrahydrocannabinol, cannabidiol, and tetrahydrocannabivarin at a combined concentration of at least 80 percent by weight.

Various aspects of this patent document relate to a method to purify tetrahydrocannabinol from a non-volatile molecule, comprising: (1) providing a composition comprising tetrahydrocannabinol and a non-volatile molecule, wherein both the tetrahydrocannabinol and the non-volatile molecule are in a liquid phase; (2) contacting the composition with energy to convert the tetrahydrocannabinol in the liquid phase into vaporized tetrahydrocannabinol in a gas phase without vaporizing the non-volatile molecule, wherein contacting the composition with the energy comprises contacting the composition at least 500 joules and no greater than 2500 joules of energy per gram of the composition; (3) separating the vaporized tetrahydrocannabinol in the gas phase from the non-volatile molecule; (4) contacting the vaporized tetrahydrocannabinol with a heat sink less than 360 seconds after converting the tetrahydrocannabinol in the liquid phase into the vaporized tetrahydrocannabinol in the gas phase to condense the vaporized tetrahydrocannabinol into condensed tetrahydrocannabinol in a liquid distillate that comprises (i) tetrahydrocannabinol at a concentration of at least 70 percent and no greater than 95 percent by weight; (ii) cannabidiol at a concentration of at least 0.5 percent and no greater than 25 percent by weight; (iii) tetrahydrocannabivarin at a concentration of at least 0.5 percent and no greater than 25 percent by weight; and (iv) tetrahydrocannabinol and cannabinol at a molar ratio greater than 100:1; and (5) collecting the liquid distillate.

Various aspects of this patent document relate to a method to purify tetrahydrocannabinol from a non-volatile molecule, comprising: (1) providing a composition comprising tetrahydrocannabinol and a non-volatile molecule, wherein both the tetrahydrocannabinol and the non-volatile molecule are in a liquid phase; (2) contacting the composition at least 5 kilojoules and no greater than 50 kilojoules of energy per gram of the composition to convert the tetrahydrocannabinol in the liquid phase into vaporized tetrahydrocannabinol in a gas phase without vaporizing the non-volatile molecule; (3) separating the vaporized tetrahydrocannabinol in the gas phase from the non-volatile molecule; (4) contacting the vaporized tetrahydrocannabinol with a heat sink less than 360 seconds after converting the tetrahydrocannabinol in the liquid phase into the vaporized tetrahydrocannabinol in the gas phase to condense the vaporized tetrahydrocannabinol into condensed tetrahydrocannabinol in a liquid distillate that comprises (i) tetrahydrocannabinol at a concentration of at least 70 percent and no greater than 95 percent by weight; (ii) cannabidiol at a concentration of at least 0.5 percent and no greater than 25 percent by weight; (iii) tetrahydrocannabivarin at a concentration of at least 0.5 percent and no greater than 25 percent by weight; and (iv) tetrahydrocannabinol and cannabinol at a molar ratio greater than 100:1; and (5) collecting the liquid distillate. In some specific embodiments, the method comprises contacting the composition at least 5 kilojoules and no greater than 25 kilojoules of energy per gram of the composition. In some very specific embodiments, the method comprises contacting the composition at least 5 kilojoules and no greater than 7 kilojoules of energy per gram of the composition.

DETAILED DESCRIPTION

Figure 1:
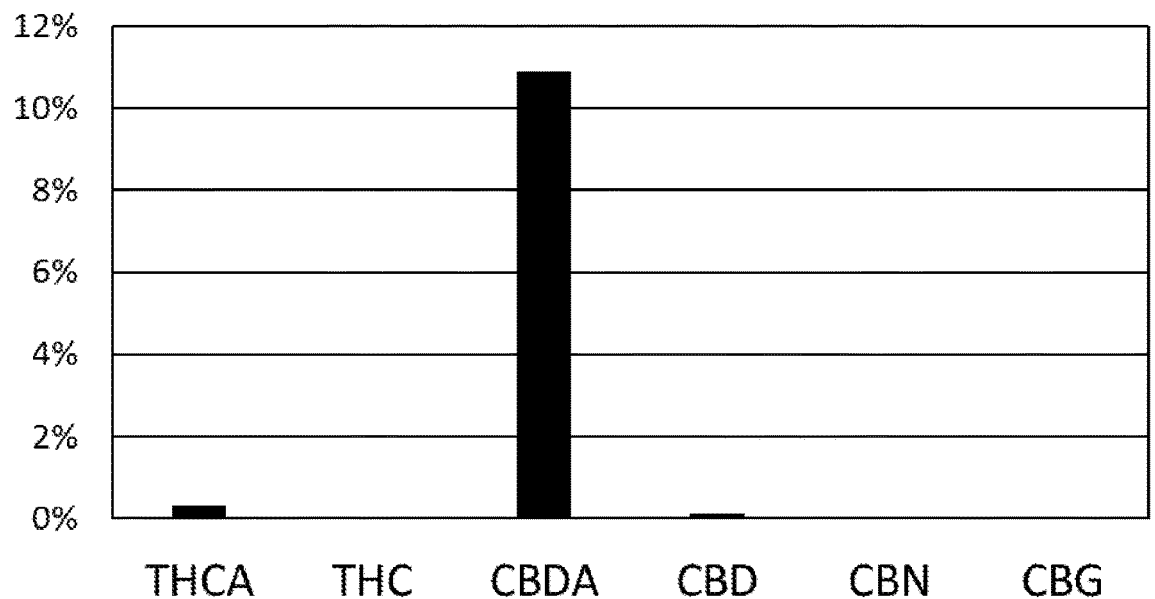
FIG. 1 is a bar graph depicting the THCA, THC, CBDA, CBD, CBN, and CBG concentrations found in a typical sample of USDA organic industrial hemp.

Various aspects of the disclosure relate to a method to purify a cannabinoid molecule from a non-volatile molecule.

In some embodiments, a method comprises providing a composition comprising a cannabinoid molecule and a non-volatile molecule. In some specific embodiments, a method comprises providing a composition comprising a cannabinoid molecule and a non-volatile molecule in which both the cannabinoid molecule and the non-volatile molecule are in a liquid phase or a solid phase.

In some embodiments, a method comprises contacting a composition with 50 joules to 100 kilojoules of energy per gram of the composition. In some specific embodiments, a method comprises contacting a composition with 50 joules to 100 kilojoules of energy per gram of the composition to convert a cannabinoid molecule of the composition into a vaporized cannabinoid molecule in a gas phase. In some very specific embodiments, a method comprises contacting a composition with 50 joules to 100 kilojoules of energy per gram of the composition to convert a cannabinoid molecule of the composition into a vaporized cannabinoid molecule in a gas phase without vaporizing a non-volatile molecule of the composition.

In some embodiments, a method comprises separating a vaporized cannabinoid molecule in a gas phase from a non-volatile molecule.

In some specific embodiments, a method comprises contacting a vaporized cannabinoid molecule with a heat sink to condense the vaporized cannabinoid molecule into a condensed cannabinoid molecule in a liquid distillate.

In some embodiments, a composition comprises a plant material. In some specific embodiments, a composition comprises a ground plant material. In some embodiments, a composition has a surface-area-to-volume ratio greater than 1000 per meter.

In some embodiments, a plant material is a species of the genus *Cannabis*. In some specific embodiments, a plant material is *Cannabis sativa*. In some specific embodiments, a plant material is *Cannabis* indica. In some specific embodiments, a plant material is *Cannabis ruderalis*. In some very specific embodiments, a plant material is *Cannabis sativa* forma indica. In some specific embodiments, a plant material lacks THC and potential THC at a combined concentration by weight exceeding 0.3%. The term "potential THC" refers to THCA multiplied by 314.47 (the molecular weight of THC) and divided by 358.48 (the molecular weight of THCA). A plant material that lacks THC and contains 0.33% THCA, for example, contains THC and potential THCA at a combined concentration by weight of 0.29%.

In some embodiments, a composition comprises an extracted oil from the genus *Cannabis*. In some specific embodiments, a composition comprises an extracted oil from industrial hemp. The term "industrial hemp" refers to *Cannabis sativa* forma indica that either is essentially free of THC and THCA or comprises THC and potential THC at a combined concentration by weight no greater than 0.3%.

In some embodiments, a composition comprises marijuana or a composition is derived from marijuana.

In some embodiments, a composition is a liquid such as an oil. In some embodiments, a composition is an aerosol. In some specific embodiments, a composition comprises a suspension of solid particles in a gas. In some specific embodiments, a composition comprises a suspension of liquid droplets in a gas.

In some specific embodiments, a composition comprises a powder. In some specific embodiments, a composition comprises crystals. In some specific embodiments, a composition comprises wax.

In some embodiments, a composition is suspended in a gas phase.

In some embodiments, a method comprises grinding plant material.

In some embodiments, a method comprises separating particles of industrial hemp, marijuana, or other plant material by size such as by using a screen, mesh, or particle classifier.

In some embodiments, a cannabinoid molecule, vaporized cannabinoid molecule, or condensed cannabinoid molecule is selected from one or more of THCA, tetrahydrocannabivarin carboxylic acid ("THCVA"), tetrahydrocannabiorcolic acid ("THCOA"), CBDA, CBDVA, cannabidiorcolic acid ("CBDOA"), cannabichromenic acid ("CBCA"), cannabichromevarinic acid ("CBCVA"), cannabigerolic acid ("CBGA"), cannabigerovarinic acid ("CBGVA"), cannabicyclolic acid ("CBLA"), cannabielsoic acid ("CBEA"), perrottetinenic acid, carboxylates of any of the preceding molecules, naturally-occurring ethers of any of the preceding molecules, and stereoisomers of any one of the preceding molecules.

In some embodiments, a cannabinoid molecule, modified cannabinoid molecule, vaporized cannabinoid molecule, or condensed cannabinoid molecule is selected from one or more of THC, tetrahydrocannabivarin ("THCV"), tetrahydrocannabiorcol ("THCO"), CBD, CBDV, cannabidiorcol, ("CBDO"), cannabichromene ("CBC"), cannabichromevarin ("CBCV"), cannabigerol ("CBG"), cannabigerovarin ("CBGV"), cannabicyclol ("CBL"), cannabielsoin ("CBE"), perrottetinene, naturally-occurring ethers of any of the preceding molecules, and stereoisomers of any of the preceding molecules.

In some specific embodiments, a cannabinoid molecule, vaporized cannabinoid molecule, or condensed cannabinoid molecule is CBDA. In some specific embodiments, a cannabinoid molecule, vaporized cannabinoid molecule, or condensed cannabinoid molecule is CBDVA, which is also known as 2,4-dihydroxy-3-[(1R,6R)-6-isopropenyl-3-methylcyclohex-2-en-1-yl]-6-propylbenzoic acid. In some specific embodiments, a cannabinoid molecule, vaporized cannabinoid molecule, or condensed cannabinoid molecule is THCA. In some specific embodiments, a cannabinoid molecule, vaporized cannabinoid molecule, or condensed cannabinoid molecule is THCVA, which is also known as (6aR,10aR)-1-hydroxy-6,6,9-trimethyl-3-propyl-6a,7,8,10a-tetrahydro-6H-benzo[c]chromene-2-carboxylic acid.

In some specific embodiments, a modified cannabinoid molecule, vaporized cannabinoid molecule, or condensed cannabinoid molecule is CBD, which is also known as 2-[(1R,6R)-6-isopropenyl-3-methylcyclohex-2-en-1-yl]-5-pentylbenzene-1,3-diol. In some very specific embodiments, a modified cannabinoid molecule is CBD. In some very specific embodiments, a vaporized cannabinoid molecule is CBD. In some very specific embodiments, a condensed cannabinoid molecule is CBD.

In some specific embodiments, a modified cannabinoid molecule, vaporized cannabinoid molecule, or condensed cannabinoid molecule is CBDV, which is also known as 2-[(1R,6R)-6-isopropenyl-3-methylcyclohex-2-en-1-yl]-5-propylbenzene-1,3-diol. In some very specific embodiments, a modified cannabinoid molecule is CBDV. In some very specific embodiments, a vaporized cannabinoid molecule is CBDV. In some very specific embodiments, a condensed cannabinoid molecule is CBDV.

In some specific embodiments, a modified cannabinoid molecule, vaporized cannabinoid molecule, or condensed cannabinoid molecule is THC, which is also known as (6aR,10aR)-6,6,9-trimethyl-3-pentyl-6a,7,8,10a-tetrahydro-6H-benzo[c]chromen-1-ol. In some very specific embodiments, a modified cannabinoid molecule is THC. In some very specific embodiments, a vaporized cannabinoid molecule is THC. In some very specific embodiments, a condensed cannabinoid molecule is THC.

In some specific embodiments, a modified cannabinoid molecule, vaporized cannabinoid molecule, or condensed cannabinoid molecule is THCV, which is also known as (6aR,10aR)-6,6,9-trimethyl-3-propyl-6a,7,8,10a-tetrahydro-6H-benzo[c]chromen-1-ol. In some very specific embodiments, a modified cannabinoid molecule is THCV. In some very specific embodiments, a vaporized cannabinoid molecule is THCV. In some very specific embodiments, a condensed cannabinoid molecule is THCV.

In some specific embodiments, a modified cannabinoid molecule, vaporized cannabinoid molecule, or condensed cannabinoid molecule is perrottetinene, which is also known as (6aS,10aR)-6,6,9-trimethyl-3-(2-phenylethyl)-6a,7,8,10a-tetrahydro-6H-benzo[c]chromen-1-ol. In some very specific embodiments, a modified cannabinoid molecule is perrottetinene. In some very specific embodiments, a vaporized cannabinoid molecule is perrottetinene. In some very specific embodiments, a condensed cannabinoid molecule is perrottetinene.

In some specific embodiments, a cannabinoid molecule is THCA or THC, a vaporized cannabinoid molecule is THC, and a condensed cannabinoid molecule is THC.

In some specific embodiments, a cannabinoid molecule is THCVA or THCV, a vaporized cannabinoid molecule is THCV, and a condensed cannabinoid molecule is THCV.

In some specific embodiments, a cannabinoid molecule is THCOA or THCO, a vaporized cannabinoid molecule is THCO, and a condensed cannabinoid molecule is THCO.

In some specific embodiments, a cannabinoid molecule is CBDA or CBD, a vaporized cannabinoid molecule is CBD, and a condensed cannabinoid molecule is CBD.

In some specific embodiments, a cannabinoid molecule is CBDVA or CBDV, a vaporized cannabinoid molecule is CBDV, and a condensed cannabinoid molecule is CBDV.

In some specific embodiments, a cannabinoid molecule is CBDOA or CBDO, a vaporized cannabinoid molecule is CBDO, and a condensed cannabinoid molecule is CBDO.

In some specific embodiments, a cannabinoid molecule is CBCA or CBC, a vaporized cannabinoid molecule is CBC, and a condensed cannabinoid molecule is CBC.

In some specific embodiments, a cannabinoid molecule is CBCVA or CBCV, a vaporized cannabinoid molecule is CBCV, and a condensed cannabinoid molecule is CBCV.

In some specific embodiments, a cannabinoid molecule is CBGA or CBG, a vaporized cannabinoid molecule is CBG, and a condensed cannabinoid molecule is CBG.

In some specific embodiments, a cannabinoid molecule is CBGVA or CBGV, a vaporized cannabinoid molecule is CBGV, and a condensed cannabinoid molecule is CBGV.

In some specific embodiments, a cannabinoid molecule is CBLA or CBL, a vaporized cannabinoid molecule is CBL, and a condensed cannabinoid molecule is CBL.

In some specific embodiments, a cannabinoid molecule is CBEA or CBE, a vaporized cannabinoid molecule is CBE, and a condensed cannabinoid molecule is CBE.

In some specific embodiments, a cannabinoid molecule is perrottetinenic acid or perrottetinene, a vaporized cannabinoid molecule is perrottetinene, and a condensed cannabinoid molecule is perrottetinene.

In some embodiments, a composition comprises CBDA, CBDVA, THCA, THCVA, and CBGA at a concentration of at least 6% by weight. In some embodiments, a composition comprises CBDA, CBDVA, THCA, THCVA, and CBGA at a combined concentration of 5% to 30%, 10% to 35%, or 15% to 40% by weight.

In some embodiments, a composition comprises CBDA at a concentration of at least 6% by weight. In some embodiments, a composition comprises CBDA at a concentration of 5% to 30%, 10% to 35%, or 15% to 40% by weight.

In some embodiments, a composition comprises CBDVA at a concentration of at least 0.2% by weight such. In some embodiments, a composition comprises CBDVA at a concentration of 0.1% to 5% by weight, In some embodiments, a composition comprises THCA at a concentration of at least 15% by weight. In some embodiments, a composition comprises THCA at a concentration of 5% to 30%, 10% to 35%, or 15% to 40% by weight.

In some embodiments, a composition comprises THCVA at a concentration of at least 0.2% by weight. In some embodiments, a composition comprises THCVA at a concentration of 0.1% to 5% by weight, In some embodiments, a method comprises suspending a particle of a composition comprising cannabinoids in a gas phase, in which the particle comprises a cannabinoid molecule in a liquid phase or in a solid phase. In some specific embodiments, a composition comprising a cannabinoid molecule in a liquid phase or a solid phase is contacted with sufficient energy to convert the cannabinoid molecule in the liquid phase or the solid phase into a vaporized cannabinoid molecule in a gas phase while a particle of the composition comprising the cannabinoid molecule in the liquid phase or the solid phase is suspended in the gas phase.

In some embodiments, a method comprises suspending a plurality of particles of a composition comprising cannabinoids in a gas phase, in which the plurality of particles comprises a cannabinoid molecule in a liquid phase or in a solid phase. In some specific embodiments, a composition comprising a cannabinoid molecule in a liquid phase or in a solid phase is contacted with sufficient energy to convert the cannabinoid molecule in the liquid phase or the solid phase into a vaporized cannabinoid molecule in a gas phase while a plurality of particles of the composition comprising the cannabinoid molecule in the liquid phase or the solid phase is suspended in the gas phase.

In some embodiments, a method comprises suspending a droplet of a composition comprising cannabinoids in a gas phase, in which the droplet comprises a cannabinoid molecule in a liquid phase or in a solid phase. In some specific embodiments, a composition comprising a cannabinoid molecule in a liquid phase or in a solid phase is contacted with sufficient energy to convert the cannabinoid molecule in the liquid phase or the solid phase into a vaporized cannabinoid molecule in a gas phase while a droplet of the composition comprising the cannabinoid molecule in the liquid phase or the solid phase is suspended in the gas phase.

In some embodiments, a method comprises suspending a plurality of droplets of a composition comprising cannabinoids in a gas phase, in which the plurality of droplets comprises a cannabinoid molecule in a liquid phase or in a solid phase. In some specific embodiments, a composition comprising a cannabinoid molecule in a liquid phase or a solid phase is contacted with sufficient energy to convert the cannabinoid molecule in the liquid phase or the solid phase into a vaporized cannabinoid molecule in a gas phase while a plurality of droplets of the composition comprising the cannabinoid molecule in the liquid phase or the solid phase is suspended in the gas phase.

In some embodiments, a gas phase comprises water vapor at a concentration of at least 5% by volume. In some embodiments, a gas phase comprises ethanol vapor at a concentration of at least 5% by volume. A percentage of a gas phase by volume, as described in this patent document, is calculated by dividing the partial pressure of a species of gas, such as molecular oxygen, by the total pressure of the gas phase and then multiplying the result by 100%. Solids and liquids lack any percentage by volume of a gas phase by definition. In some embodiments, a gas phase comprises molecular nitrogen, ethanol vapor, water vapor, carbon dioxide, noble gases, cannabinoids, terpenes, terpene alcohols, and terpenoids at a total concentration of at least 95% by volume.

In some embodiments, converting a cannabinoid molecule in a liquid phase or a solid phase into a vaporized cannabinoid molecule in a gas phase comprises contacting a composition comprising the cannabinoid molecule with less than 100 kilojoules ("kJ") of energy per gram of the composition.

In some embodiments, converting a cannabinoid molecule in a liquid phase or a solid phase into a vaporized cannabinoid molecule in a gas phase comprises contacting a composition comprising the cannabinoid molecule with 2 kJ to 50 kJ of energy per gram of the composition. In some very specific embodiments, converting a cannabinoid molecule in a liquid phase or a solid phase into a vaporized cannabinoid molecule in a gas phase comprises contacting a composition comprising the cannabinoid molecule with 2 kJ to 4 kJ per gram of the composition.

In some embodiments, converting a cannabinoid molecule in a liquid phase or a solid phase into a vaporized cannabinoid molecule in a gas phase comprises contacting a composition comprising the cannabinoid molecule with less than 100 kilowatts ("kW") of power per gram of the composition for less than 60 seconds. In some specific embodiments, converting a cannabinoid molecule in a liquid phase or a solid phase into a vaporized cannabinoid molecule in a gas phase comprises contacting a composition comprising the cannabinoid molecule with 1 kW to 100 kW of power per gram of the composition for 0.2 to 20 seconds.

In some embodiments, a method comprises irradiating a composition, convectively heating a composition, or conductively heating a composition, in which contacting a composition with sufficient energy comprises one or more of irradiating the composition, convectively heating the composition, or conductively heating the composition. Suitable methods of irradiating a composition are described, for example, in PCT Patent Application Publication No. WO 2018/102711 A1, which is incorporated by reference in its entirety. Suitable methods of convectively heating a composition are described, for example, in PCT Patent Application Publication No. WO 2015/049585 A2, which is incorporated by reference in its entirety. Suitable methods of conductively heating a composition are described, for example, in PCT Patent Application Publication No. WO 2016/161420 A1 and WO 2017/192527 A1, each of which is incorporated by reference in its entirety.

In some embodiments, a method comprises contacting a composition with a heated gas. In some specific embodiments, a method comprises contacting a composition with a heated gas having a temperature of 190° C. to 250° C. In some embodiments, a method comprises contacting a composition with a heated surface. In some specific embodiments, a method comprises contacting a composition with a heated surface having a temperature of 190° C. to 250° C.

In some embodiments, a method comprises coating a surface or heated surface with a composition comprising cannabinoids at a surface-area-to-volume ratio of the composition that is greater than 500 per meter prior to converting a cannabinoid molecule in a liquid phase or a solid phase into a vaporized cannabinoid molecule in a gas phase. In some specific embodiments, a composition is contacted with sufficient energy to convert a cannabinoid molecule in a liquid phase or a solid phase into a vaporized cannabinoid molecule in a gas phase while the composition is coated on a surface or heated surface at a surface-area-to-volume ratio of the composition that is greater than 500 per meter.

In some embodiments, a method comprises directing a composition comprising cannabinoids along a path having a length of at least 4 meters, in which the composition is contacted with sufficient energy to convert a cannabinoid molecule in a liquid phase or a solid phase into a vaporized cannabinoid molecule in a gas phase while the composition is being directed along the path. In some embodiments, a path has a length of 4 meters to 40 meters. Increasing the length of a path increases the probability that a first cannabinoid molecule will interact with either a second cannabinoid molecule or other catalyst with an appropriate orientation to catalyze the decarboxylation of the first cannabinoid molecule.

In some embodiments, a method comprises directing a composition along a path having a length of at least 4 meters at a rate of at least 2 meters per second. Directing a composition along a path of a specific length at a specific rate can control the amount of energy that contacts the composition. In some embodiments, a path comprises one or more surfaces, and a method comprises heating the one or more surfaces to a temperature of 190° C. to 250° C.

In some embodiments, a composition comprises a non-volatile molecule, and a method comprises separating a vaporized cannabinoid molecule in a gas phase from a non-volatile molecule. In some specific embodiments, separating a vaporized cannabinoid molecule in a gas phase from a non-volatile molecule is performed after converting a cannabinoid molecule in a liquid phase or a solid phase into the vaporized cannabinoid molecule in the gas phase. In some specific embodiments, separating a vaporized cannabinoid molecule in a gas phase from a non-volatile molecule is performed prior to contacting the vaporized cannabinoid molecule with a heat sink. In some very specific embodiments, a method comprises separating a vaporized cannabinoid molecule in a gas phase from a non-volatile molecule by directing the gas phase through a cyclone. In some very specific embodiments, a method comprises separating a vaporized cannabinoid molecule in a gas phase from a non-volatile molecule by directing the gas phase through a filter such as an air filter. In some specific embodiments, a method comprises collecting a non-volatile molecule.

In some embodiments, a method converts less than 2% of a cannabinoid molecule of a composition into cannabinol (which is also known as 6,6,9-trimethyl-3-pentyl-benzo[c]chromen-1-ol) by mole. In some very specific embodiments, a method comprises producing a liquid distillate comprising a condensed cannabinoid molecule and cannabinol at a molar ratio greater than 50:1.

In some specific embodiments, a composition comprises CBDA, and a method converts less than 2% of the CBDA of the composition into cannabinol by mole. In some very specific embodiments, a method comprises producing a liquid distillate comprising CBD and cannabinol at a molar ratio greater than 50:1.

In some specific embodiments, a composition comprises THCA, and a method converts less than 2% of the THCA of the composition into cannabinol by mole. In some very specific embodiments, a method comprises producing a liquid distillate comprising THC and cannabinol at a molar ratio greater than 50:1.

In some embodiments, a method converts less than 0.2% of a cannabinoid molecule of a composition into 6,6,9-trimethyl-3-pentyl-6a,7,10,10a-tetrahydro-6H-benzo[c]chromen-1-ol ("Δ8-THC" or "delta-8-tetrahydrocannabinol") by mole. In some very specific embodiments, a method comprises producing a liquid distillate comprising a condensed cannabinoid molecule and Δ8-THC at a molar ratio greater than 500:1.

In some specific embodiments, a composition comprises CBDA, and a method converts less than 2% of the CBDA of the composition into Δ8-THC by mole. In some very specific embodiments, a method comprises producing a liquid distillate comprising CBD and Δ8-THC at a molar ratio greater than 500:1.

In some specific embodiments, a composition comprises THCA, and a method converts less than 2% of the THCA of the composition into Δ8-THC by mole. In some very specific embodiments, a method comprises producing a liquid distillate comprising THC and Δ8-THC at a molar ratio greater than 500:1.

In some embodiments, a heat sink has a surface area greater than 10% of the surface area of a composition comprising cannabinoids. A heat sink having a relatively large surface area allows for rapid condensation. In some specific embodiments, a heat sink is a colloid comprising a gas-phase dispersion medium. In some very specific embodiments, a heat sink is an aerosol or a foam. In some very specific embodiments, a heat sink is a spray. Colloids such as aerosols and foams generally have large surface areas, and colloids are therefore suitable heat sinks.

In some embodiments, a heat sink comprises a volatile liquid. Heat sinks comprising a volatile liquid are particularly useful because the vaporization of a volatile liquid can absorb a large amount of energy. In some specific embodiments, a heat sink comprises a volatile liquid, and the volatile liquid comprises one or both of ethanol and water. In some very specific embodiments, a heat sink comprises a volatile liquid, and the volatile liquid comprises ethanol and water at a combined concentration by weight of at least 90%.

In some embodiments, contacting a vaporized cannabinoid molecule with a heat sink comprises passive cooling such as by exposing the vaporized cannabinoid molecule or a container comprising the vaporized cannabinoid molecule to ambient temperature. In some specific embodiments, exposing a vaporized cannabinoid molecule or a container comprising the vaporized cannabinoid molecule to ambient temperature comprises cooling in an autoclave. In some specific embodiments, exposing a vaporized cannabinoid molecule to ambient temperature comprises directing the vaporized cannabinoid molecule through a fluid-cooled condenser.

In some embodiments, a method comprises contacting a vaporized cannabinoid molecule with a heat sink less than 20 seconds after converting a cannabinoid molecule in a liquid phase or a solid phase into the vaporized cannabinoid molecule in a gas phase.

In some embodiments, a method comprises condensing a vaporized cannabinoid molecule into a condensed cannabinoid molecule less than 20 seconds after converting a cannabinoid molecule in a liquid phase or a solid phase into the vaporized cannabinoid molecule in a gas phase. Cannabinoid vapor can be converted into condensed cannabinoids about 2 seconds after vaporization with excellent yields of decarboxylated cannabinoids when a composition comprising cannabinoids is a plant material having a surface-area-to-volume ratio and water content as described in this patent document.

In some specific embodiments, a method comprises producing a liquid distillate comprising cannabinol at a concentration less than 0.8% by weight. In some very specific embodiments, a method comprises producing a liquid distillate comprising one or both of CBD and THC at a concentration greater than 6% by weight and cannabinol at a concentration less than 0.8% by weight.

In some embodiments, a method comprises converting at least 95% of a cannabinoid molecule of a composition into a vaporized cannabinoid molecule in a gas phase by mole. In some embodiments, a method comprises producing a liquid distillate comprising cannabinoids, and less than 2% of the cannabinoids of the liquid distillate comprise a carboxyl group.

In some embodiments, a method comprises producing a liquid distillate comprising condensed cannabinoid molecules selected from one, two, three, four, or each of CBD, CBDV, THC, THCV, and CBG. In some specific embodiments, a method comprises producing a liquid distillate comprising condensed cannabinoid molecules in which at least 95% of the condensed cannabinoid molecules of the liquid distillate are CBD, CBDV, THC, THCV, and CBG by weight.

In some embodiments, a method comprises producing a liquid distillate comprising ethanol. In some specific embodiments, a method comprises producing a liquid distillate comprising water and ethanol at a combined concentration of at least 50% by weight. Ethanol reduces the viscosity of a liquid distillate which allows for improved automation of the purification methods.

In some embodiments, a liquid distillate comprises a non-cannabinoid molecule and a condensed cannabinoid molecule, and a method comprises separating the non-cannabinoid molecule from the condensed cannabinoid molecule to produce a product. In some embodiments, a liquid distillate comprises a non-cannabinoid molecule and a condensed cannabinoid molecule, and a method comprises separating the non-cannabinoid molecule from the condensed cannabinoid molecule to produce a product comprising the condensed cannabinoid molecule at a concentration of at least 60% by weight. In some embodiments, a liquid distillate comprises a non-cannabinoid molecule and a condensed cannabinoid molecule, and a method comprises separating the non-cannabinoid molecule from the condensed cannabinoid molecule to produce a product comprising the condensed cannabinoid molecule at a concentration of 55% to 65%, 60% to 70%, 65% to 75%, 70% to 80%, 75% to 85%, 80% to 90%, 85% to 95%, or 90% to 99.9% by weight.

In some embodiments, a liquid distillate comprises a non-cannabinoid molecule and CBD, and a method comprises separating the non-cannabinoid molecule from the CBD to produce a product comprising the CBD at a concentration of at least 60% by weight. In some embodiments, a liquid distillate comprises a non-cannabinoid molecule and CBD, and a method comprises separating the non-cannabinoid molecule from the CBD to produce a product comprising the CBD at a concentration of 55% to 65%, 60% to 70%, 65% to 75%, 70% to 80%, 75% to 85%, 80% to 90%, 85% to 95%, or 90% to 99.9% by weight.

In some embodiments, a liquid distillate comprises a non-cannabinoid molecule and CBDV, and a method comprises separating the non-cannabinoid molecule from the CBDV to produce a product comprising the CBDV at a concentration of at least 0.2% by weight. In some embodiments, a liquid distillate comprises a non-cannabinoid molecule and CBDV, and a method comprises separating the non-cannabinoid molecule from the CBDV to produce a product comprising the CBDV at a concentration of 0.1% to 10% by weight.

In some embodiments, a liquid distillate comprises a non-cannabinoid molecule, CBD, and CBDV, and a method comprises separating the non-cannabinoid molecule from the CBD and CBDV to produce a product comprising the CBD and CBDV at a combined concentration of at least 60% by weight. In some embodiments, a liquid distillate comprises a non-cannabinoid molecule, CBD, and CBDV, and a method comprises separating the non-cannabinoid molecule from the CBD and CBDV to produce a product comprising the CBD and CBDV at a combined concentration of 55% to 65%, 60% to 70%, 65% to 75%, 70% to 80%, 75% to 85%, 80% to 90%, 85% to 95%, or 90% to 99.9% by weight.

In some embodiments, a liquid distillate comprises a non-cannabinoid molecule and THC, and a method comprises separating the non-cannabinoid molecule from the THC to produce a product comprising the THC at a concentration of at least 60% by weight. In some embodiments, a liquid distillate comprises a non-cannabinoid molecule and THC, and a method comprises separating the non-cannabinoid molecule from the THC to produce a product comprising the THC at a concentration of 55% to 65%, 60% to 70%, 65% to 75%, 70% to 80%, 75% to 85%, 80% to 90%, 85% to 95%, or 90% to 99.9% by weight.

In some embodiments, a liquid distillate comprises a non-cannabinoid molecule and THCV, and a method comprises separating the non-cannabinoid molecule from the THCV to produce a product comprising the THCV at a concentration of at least 0.2% by weight. In some embodiments, a liquid distillate comprises a non-cannabinoid molecule and THCV, and a method comprises separating the non-cannabinoid molecule from the THCV to produce a product comprising the THCV at a concentration of 0.1% to 10% by weight.

In some embodiments, a liquid distillate comprises a non-cannabinoid molecule, THC, and THCV, and a method comprises separating the non-cannabinoid molecule from the THC and THCV to produce a product comprising the THC and THCV at a combined concentration of at least 60% by weight. In some embodiments, a liquid distillate comprises a non-cannabinoid molecule, THC, and THCV, and a method comprises separating the non-cannabinoid molecule from the THC and THCV to produce a product comprising the THC and THCV at a combined concentration of 55% to 65%, 60% to 70%, 65% to 75%, 70% to 80%, 75% to 85%, 80% to 90%, 85% to 95%, or 90% to 99.9% by weight.

In some embodiments, a method comprises producing a product comprising cannabinoids at a concentration of at least 60% by weight. In some embodiments, a method comprises producing a product comprising a condensed cannabinoid molecule at a concentration of at least 60% by weight. In some specific embodiments, a method comprises producing a product comprising one, two, three, four, or each of CBD, CBDV, THC, THCV, and CBG at a combined concentration of at least 60% by weight.

The following examples provide a framework to implement certain aspects of the disclosure in commercially-viable processes, and these examples do not limit the scope of this patent document or any claim that matures from the disclosure of this patent document.

EXEMPLIFICATION

Example 1. Decarboxylation and Distillation of Cannabinoids from Organic Industrial Hemp Example 1 is prophetic and representative of actual methods. The method of PCT Patent Application Publication No. WO 2016/161420 A1 is performed using organic industrial hemp. The water content of the hemp is less than 10% by weight. The cannabinoid content of the hemp is about 11-12% by weight and consists of about 11% CBDA, 0.1% CBD, 0.3% THCA, and 0% THC by weight (see, for example, FIG. 1). The hemp is ground and sifted to provide a particulate having an average diameter less than 2 mm and a surface-area-to-volume ratio greater than 3000 per meter. The hemp is suspended in heated gas to vaporize the cannabinoids. The heated gas is produced by resistive heating at 10-20 kW. The oxygen content of the heated gas is significantly below the ~20% oxygen content of air by volume. Oxygen is reduced relative to air by blanketing the distillation machine in an inert gas and by evaporating water from the hemp. The heated gas and suspended hemp are directed through heated tubes having a length of 5 to 50 meters at a rate of 5 to 20 meters per second. A known mass of hemp is directed through the heated tubes at a known rate such that the hemp is exposed to less than 100 kJ of energy per gram of the hemp. The heated tubes reverse direction in Cartesian space several times to increase the number of collisions between particles and gas-phase molecules. Cannabinoid vapor is mechanically separated from suspended non-volatile molecules of the hemp using a cyclone and filters. Cannabinoid vapor is condensed approximately 1 to 5 seconds after vaporization. A liquid distillate is collected by rinsing the condensed cannabinoids from the surfaces of the heat sink with ethanol. Greater than 90% of the cannabinoids of the hemp are recovered as cannabinoids of the liquid distillate by mole. Greater than 95% of the cannabinoids of the liquid distillate are decarboxylated. A rotary evaporator is used to remove ethanol and water from the liquid distillate to produce a uniform product comprising at least 10% by weight cannabinoids.

Figure 2:
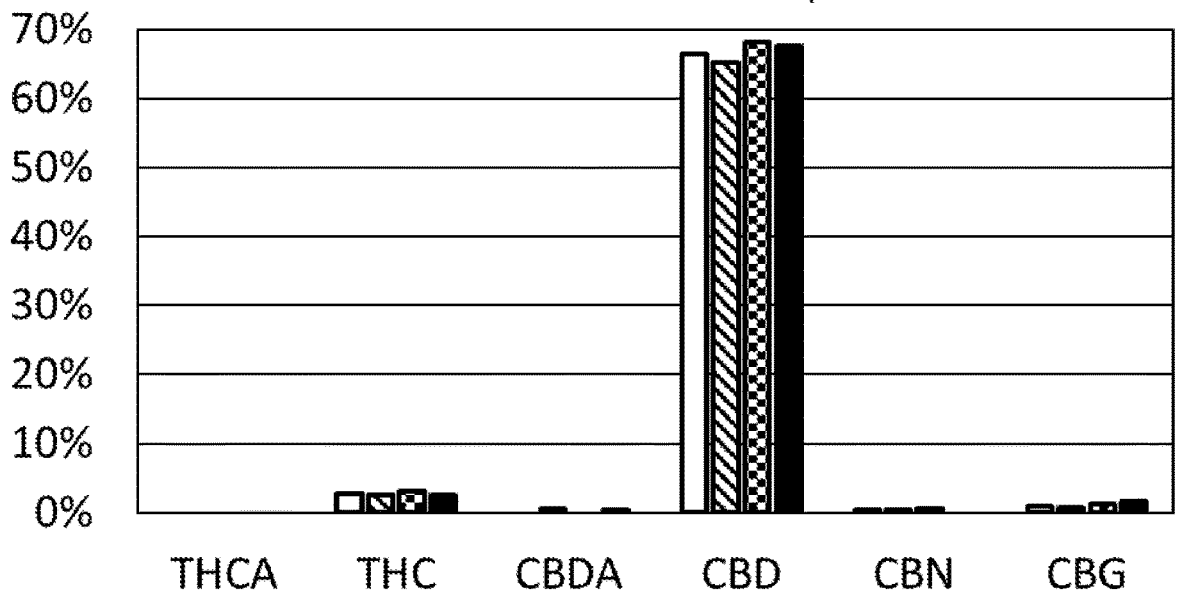
FIG. 2 is a bar graph depicting the THCA, THC, CBDA, CBD, CBN, and CBG concentrations found in four different concentrate products produced according to methods disclosed in this patent document.

Example 2. Products Produced by Decarboxylation and Distillation of Cannabinoids from Organic Industrial Hemp The method of Example 1 was performed on four different batches of organic hemp, and cannabinoid concentrations of concentrated products produced from the liquid distillates were determined by an accredited, third-party *cannabis* testing laboratory. Actual cannabinoid concentrations by weight of concentrated products produced from liquid distillates are shown in in FIG. 2 and Table 1. In each instance, greater than 99.5% of the cannabinoids of the concentrated products were decarboxylated.

TABLE 1

Actual Concentrations of Cannabinoids in Four Concentrated Products Produced from Liquid Distillate Following Decarboxylation and Distillation of the Cannabinoids from Organic Industrial Hemp

|      | 1     | 2     | 3     | 4     |
|------|-------|-------|-------|-------|
| CBD  | 66.5% | 65.2% | 68.1% | 67.6% |
| CBDA | 0.0%  | 0.6%  | 0.0%  | 0.3%  |
| THC  | 2.7%  | 2.6%  | 3.2%  | 2.6%  |
| THCA | 0.0%  | 0.0%  | 0.0%  | 0.0%  |
| CBN  | 0.4%  | 0.3%  | 0.4%  | 0.0%  |
| CBG  | 0.96% | 0.76% | 1.27% | 1.62% |

Example 3. Decarboxylation and Distillation of Cannabinoids from Organic *Cannabis*

Example 3 is prophetic and representative of actual methods. The method of PCT Patent Application Publication No. WO 2016/161420 A1 is performed using organic *cannabis*. The water content of the *cannabis* is less than 10% by weight. The cannabinoid content of the *cannabis* is about 20-30% by weight. The *cannabis* is ground and sifted to provide a particulate having an average diameter less than 2 mm and a surface-area-to-volume ratio greater than 3000 per meter. The *cannabis* is suspended in heated gas to vaporize the cannabinoids. The heated gas is produced by resistive heating at 10-20 kW. The oxygen content of the heated gas is significantly below the ~20% oxygen content of air by volume. Oxygen is reduced relative to air by blanketing the distillation machine in an inert gas and by evaporating water from the *cannabis*. The heated gas and suspended *cannabis* are directed through heated tubes having a length of 5 to 50 meters at a rate of 5 to 20 meters per second. A known mass of *cannabis* is directed through the heated tubes at a known rate such that the *cannabis* is exposed to less than 100 kJ of energy per gram of the *cannabis*. The heated tubes reverse direction in Cartesian space several times to increase the number of collisions between particles and gas-phase molecules. Cannabinoid vapor is mechanically separated from suspended non-volatile molecules of the *cannabis* using a cyclone and filters. Cannabinoid vapor is condensed approximately 1 to 5 seconds after vaporization. A liquid distillate is collected by rinsing the condensed cannabinoids from the surfaces of the heat sink with ethanol. Greater than 90% of the cannabinoids of the *cannabis* are recovered as cannabinoids of the liquid distillate by mole. Greater than 95% of the cannabinoids of the liquid distillate are decarboxylated. A rotary evaporator is used to remove ethanol and water from the liquid distillate to produce a uniform product comprising at least 10% by weight cannabinoids.

What is claimed is:
1. A method to purify tetrahydrocannabinol, comprising:
providing a composition comprising tetrahydrocannabinol and a non-volatile molecule, wherein both the tetrahydrocannabinol and the non-volatile molecule are in a liquid phase or a solid phase;
contacting the composition with 50 joules to 100 kilojoules of energy per gram of the composition to convert the tetrahydrocannabinol in the liquid phase or the solid phase into vaporized tetrahydrocannabinol in a gas phase without vaporizing the non-volatile molecule;
separating the vaporized tetrahydrocannabinol in the gas phase from the non-volatile molecule;

contacting the vaporized tetrahydrocannabinol with a heat sink to condense the vaporized tetrahydrocannabinol into condensed tetrahydrocannabinol in a liquid distillate; and collecting the liquid distillate.

2. A method to purify tetrahydrocannabinol, comprising:

providing a composition comprising tetrahydrocannabinol in a liquid phase or a solid phase;

contacting the composition with 50 joules to 100 kilojoules of energy per gram of the composition to convert the tetrahydrocannabinol in the liquid phase or the solid phase into vaporized tetrahydrocannabinol in a gas phase; and contacting the vaporized tetrahydrocannabinol with a heat sink to condense the vaporized tetrahydrocannabinol into condensed tetrahydrocannabinol.

3. The method of claim 2, wherein:

the composition comprises a non-volatile molecule;

the composition is contacted with the energy without vaporizing the non-volatile molecule;

the method comprises separating the vaporized tetrahydrocannabinol in the gas phase from the non-volatile molecule;

the method comprises condensing the vaporized tetrahydrocannabinol into a liquid distillate that comprises the condensed tetrahydrocannabinol; and the method comprises collecting the liquid distillate.

4. The method of claim 2, comprising contacting the composition with 2 kilojoules to 4 kilojoules of energy per gram of the composition.

5. The method of claim 2, wherein the composition has a surface-area-to-volume ratio of greater than 1000 per meter.

6. The method of claim 2, comprising contacting the vaporized tetrahydrocannabinol with the heat sink less than 20 seconds after converting the tetrahydrocannabinol in the liquid phase or the solid phase into the vaporized tetrahydrocannabinol.

7. The method of claim 2, wherein the vaporized tetrahydrocannabinol is condensed into the condensed tetrahydrocannabinol less than 30 seconds after the tetrahydrocannabinol is converted into the vaporized tetrahydrocannabinol.

8. The method of claim 2, comprising producing a liquid distillate that comprises the condensed tetrahydrocannabinol and cannabinol at a molar ratio of greater than 100:1.

9. The method of claim 2, wherein the method converts less than 5% of the tetrahydrocannabinol of the composition into cannabinol.

10. The method of claim 2, comprising producing a liquid distillate that comprises the condensed tetrahydrocannabinol and delta-8-tetrahydrocannabinol at a molar ratio of greater than 300:1.

11. The method of claim 2, wherein the method converts less than 5% of the tetrahydrocannabinol of the composition into delta-8-tetrahydrocannabinol.

12. The method of claim 2, comprising contacting the composition with 2 kilojoules to 50 kilojoules of energy per gram of the composition.

13. The method of claim 12, comprising coating a heated surface with the composition at a surface-area-to-volume ratio of the composition that is greater than 500 per meter ($m^{-1}$), wherein the composition is contacted with the 2 kilojoules to 50 kilojoules of energy per gram of the composition when the heated surface is coated with the composition.

14. The method of claim 12, wherein contacting the composition with the 2 kilojoules to 50 kilojoules of energy per gram of the composition is performed in a short-path distillation apparatus.

15. The method of claim 2, comprising contacting the composition with a heated surface having a temperature of 330° F. to 450° F.

16. The method of claim 2, wherein the composition comprises water at a concentration of less than 10% by weight.

17. The method of claim 2, wherein the composition comprises an extracted oil from the genus *Cannabis*.

18. The method of claim 2, wherein converting the tetrahydrocannabinol in the liquid phase or the solid phase into the vaporized tetrahydrocannabinol in the gas phase comprises contacting the composition with 10 watts to 100 kilowatts of power per gram of the composition for 0.1 to 60 seconds.

19. The method of claim 18, wherein:

the composition comprises cannabidiolic acid; and the method comprises contacting the composition with energy at a rate of less than 100 kilowatts of power.

20. A method to purify tetrahydrocannabinol, comprising:

providing a composition comprising tetrahydrocannabinol in a liquid phase or a solid phase, wherein the composition has a surface-area-to-volume ratio that is greater than 1000 per meter ($m^{-1}$);

contacting the composition with 50 joules to 100 kilojoules of energy per gram of the composition to convert the tetrahydrocannabinol in the liquid phase or the solid phase into vaporized tetrahydrocannabinol in a gas phase; and contacting the vaporized tetrahydrocannabinol with a heat sink to condense the vaporized tetrahydrocannabinol into condensed tetrahydrocannabinol.

* * * * *